United States Patent [19]

Steinmann

[11] Patent Number: 5,024,916
[45] Date of Patent: Jun. 18, 1991

[54] ORGANOMETAL-CONTAINING POLYMERS AND USE THEREOF IN A PHOTOSENSITIVE COMPOSITION WITH PHOTOACID GENERATORS

[75] Inventor: Alfred Steinmann, Praroman, Switzerland

[73] Assignee: CIBA-GEIGY Corporation, Ardsley, N.Y.

[21] Appl. No.: 587,293

[22] Filed: Sep. 24, 1990

Related U.S. Application Data

[62] Division of Ser. No. 237,472, Aug. 29, 1988, Pat. No. 4,965,316.

[30] Foreign Application Priority Data

Sep. 7, 1987 [CH] Switzerland ............... 3426/87

[51] Int. Cl.$^5$ .............................. G03C 1/76
[52] U.S. Cl. ........................... 430/270; 430/326; 430/914
[58] Field of Search ............ 430/326, 270, 914

[56] References Cited

U.S. PATENT DOCUMENTS

| | | | |
|---|---|---|---|
| 4,486,577 | 12/1984 | Mueller et al. | |
| 4,689,289 | 8/1987 | Crivello | 430/270 |
| 4,752,552 | 6/1988 | Aoai | 430/270 |
| 4,788,127 | 11/1988 | Bailey et al. | 430/270 |
| 4,842,986 | 6/1989 | Matsuda et al. | 430/326 |
| 4,853,453 | 8/1989 | Schäfer et al. | |

*Primary Examiner*—Charles L. Bowers, Jr.
*Assistant Examiner*—John S. Y. Chu
*Attorney, Agent, or Firm*—Stephen V. O'Brien

[57] ABSTRACT

Organometal-containing polymers having side chains of the formula I

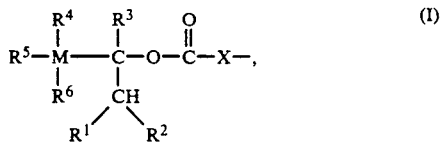

in which, for example, M is Si, X is O, $R^1$ and $R^2$ are hydrogen and $R^4$ to $R^6$ are each methyl and which have an average molecular weight between 1,000 and 1,000,000, are suitable for the preparation of dry-developable photoresists, such as are required for the generation of structured images, in particular in microelectronics.

12 Claims, No Drawings

ORGANOMETAL-CONTAINING POLYMERS AND USE THEREOF IN A PHOTOSENSITIVE COMPOSITION WITH PHOTOACID GENERATORS

This is a divisional of application Ser. No. 237,472 filed on Aug. 29, 1988, now U.S. Pat. No. 4,965,316.

The invention relates to novel organometal-containing polymers, radiation-sensitive, dry-developable, oxygen plasma-resistant compositions containing these compounds and also use thereof for the production of structured positive images.

Self- or dry-developable compositions (resists) are understood to mean a class of compounds which on irradiation disintegrate into volatile particles or can be structured in a plasma without wet development being necessary for the generation of the image. Various materials have been proposed for this purpose, for example polymethyl methacrylate, polyethylene terephthalate, nitrocellulose or polyisoprene [see, for example, H. Franke, Appl. Phys. Lett. 45(1), 110 ff (1984)]. In using these materials, various disadvantages frequently arise, such as low sensitivity, insufficient stability, formation of nonvolatile residues, insufficient resistance to oxygen plasma or insufficient resolution.

U.S. Pat. No. 4,491,628 describes resist compositions of matter containing a polymer having acid-labile side groups, for example tert-butyl ester or tert-butyl carbonate groups and a photoinitiator which upon irradiation generates an acid. The polymers used are preferably vinyl polymers such as polystyrene or polyacrylate, while the photoinitiators used are in particular onium salts, for example diaryliodonium or triarylsulfonium salts. In the exposed areas, an acid is generated and the acid-labile groups are cleaved off, thereby changing the polarity of the polymer. By choosing a suitable polar or non-polar solvent for the development of the image, both positive and negative images can be generated by means of this photoresist.

For many applications, in particular in microelectronics, the use of wet-developable resists results in some disadvantages; additional process steps, risk of contamination by the solvents, problems in waste disposal, etc. For this reason, dry-developable compositions are preferred. EP-A No. 178,208 and Microcircuit Engineering, 471–481 (1985) describe polystyrenes having silicon-containing side groups which are suitable in combination with certain photoiniators for use as dry-developable positive resists. In this process, in the irradiated areas of the resist film, trialkylsilyl groups which are bound to the polystyrene chain via ether oxygen atoms or amine nitrogen atoms are cleaved off. In this manner, the irradiated areas of the film can be removed by development in a plasma, while the nonirradiated, silicon-containing areas of the film are plasma-resistant. The disadvantage of this system is the relatively high light intensity of 80–120 mJ/cm$^2$ required for gneration of the image and also the insufficient solubility of the polymer in suitable solvents. The volatility of the silicon-containing compounds cleaved off on irradiation is also not always satisfactory.

U.S. Pat. No. 4,443,044 describes silicon-containing oxime esters of methacrylic acid, the polymers of which can also be used as dry-developable positive resists which are sensitive in the short-wave UV region. In these compounds, trimethylsilyl groups are bound directly to the benzene ring of the acetophenoneoxime radical of the polymer side chains via methylene bridges. However, this system requires a very high light intensity of 1,000–4,500 mJ/cm$^2$ to effect the removal of enough silicon-containing radicals. In addition, the system needs to be heated in a high vacuum at elevated temperature before the plasma etching process to obtain a good image structure.

A class of organometal-containing polymers has now been found which in a mixture with catalytic amounts of certain photoinitiators have a very high sensitivity to radiation. In addition, these polymers are distinguished by a high resistance to oxygen plasma. If desired, the irradiated polymers can also be developed wet, making it possible to generate not only positive but also negative images, depending on the polarity of the developer used. In addition, the compounds which are liberated and removed from the polymer side chains on irradiation are very volatile, making it unnecessary to use very high temperatures or even high vacuum for the dry development.

The invention relates to organometal-containing polymers having groupings of the formula I

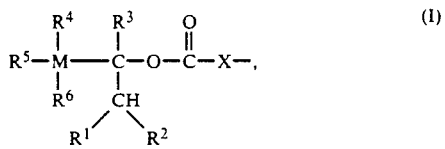

in which $R^1$ to $R^6$ independently of one another are $C_1$–$C_4$alkyl, $C_1$–$C_4$-alkoxy, phenyl, benzyl, phenoxy, a group -$M(R^8)_3$ or

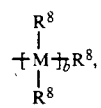

or $R^3$ and $R^4$ together are

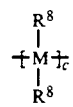

and in addition $R^1$ to $R^3$ can also be hydrogen atoms, $R^8$ is $C_1$–$C_4$alkyl, $C_1$–$C_4$alkoxy, phenyl, benzyl or phenoxy, M is Si, Ge, Sn, CH$_2$Si or OSi and X is O, S or NR', where R' is hydrogen or a single bond, b is a whole number from 1 to 6 and c is a whole number from 3 to 6, and an average molecular weight between 1,000 and 1,000,000.

Preferably, the groupings of the formula I are bound to a polystyrene polymer and thus the polymers according to the invention contain repeating units of the formula II

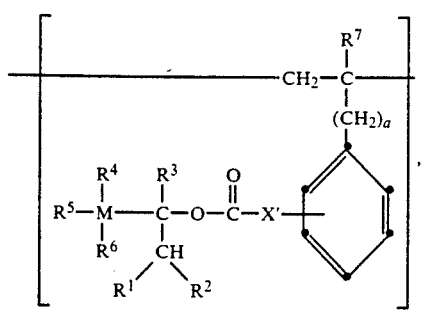
(II)

in which $R^1$ to $R^6$ and M are as defined above, X' is O, S or NH, $R^7$ is hydrogen or $C_1$-$C_4$alkyl and a is zero or 1.

The $C_1$-$C_4$alkyl groups or the alkyl radicals of the $C_1$-$C_4$alkoxy groups of the radicals $R^1$ to $R^8$ of the compounds according to the invention can be branched or preferably straight-chain and are, for example, n-, iso-, sec- or tert-butyl, n- or iso-propyl, ethyl and in particular methyl.

Particularly preferably, compounds according to the invention are silicon compounds, in which M is $CH_2Si$, OSi or in particular Si. Likewise, compounds according to the invention are preferably those in which X is S or in particular O.

The organometal-containing groupings of the formula I of the polymers according to the invention contain by definition at least one silicon, germanium or tin atom M, although they can also have two or more of these atoms. Where the substituents $R^3$ and $R^4$ together are a divalent

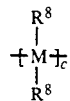

radical, the groupings form a ring which contains, for example, a carbon atom and several metal atoms. These compounds preferably contain five- and six-membered rings. Preferably, the compounds according to the invention are also those in which the radicals $R^4$, $R^5$ and $R^6$ are identical.

In general, preferance is given to those polymers according to the invention which, upon irradiation in the presence of an acid-liberating photoinitiator, eliminate a very volatile compound

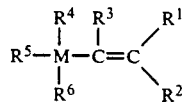

in addition to CO.

It will be readily understood that this goal can be achieved by suitable combinations of the substituents $R^1$ to $R^6$ and of the metal atom M.

Where one of the radicals $R^1$ to $R^6$ of the compounds according to the invention is

b is preferably a whole number from 1 to 3, in particular 1.

Preference is also given to polymers according to the invention in which $R^1$ and $R^2$ are each hydrogen, $R^3$ is methyl or $Si(CH_3)_3$ and $R^4$ to $R^6$ are each methyl or in which $R^3$ and $R^4$ together are

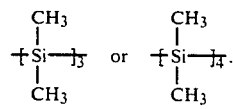

Particular preference is given to polymers in which $R^1$ and $R^2$ are each hydrogen, $R^3$ is methyl or $Si(CH_3)_3$, $R^4$ to $R^6$ are each methyl, M is Si and X is O. Preference is also given to compounds having repeating units of the formula II in which a is zero and $R^7$ is hydrogen or methyl.

The polymers according to the invention preferably have an average molecular weight from 10,000 to 500,000 and in particular from 25,000 to 100,000.

The polymers according to the invention having repeating units of the formula II are preferably homopolymers. However, the radiation-sensitive, dry-developable composition may also comprise for example copolymers which are synthesized from two or more building blocks of the formula II having different structures or copolymers which, in addition to structural units of the formula II, contain other building blocks which are derived from copolymerizable monomers. Accordingly, the present invention also relates to organometal-containing copolymers containing the repeating structural element of the formula II and up to 50 mol %, based on the entire copolymer, of structural units which are derived from other copolymerizable monomers.

Preference is given to copolymers which, in addition to structural elements of the formula II, contain at least one of the structural elements of the formulae III or IV

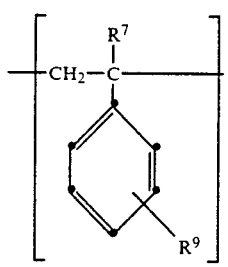
(III)

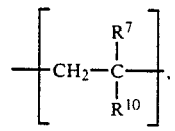
(IV)

in which $R^7$ is as defined above, $R^9$ is hydrogen $C_1$-$C_4$alkyl or $C_1$-$C_4$alkoxy and $R^{10}$ is hydrogen, $C_1$-$C_4$alkyl, $C_1$–$C_4$alkoxy, $C_1$–$C_4$alkoxycarbonyl or $C_1$–$C_4$alkylcarbonyloxy.

The $C_1$–$C_4$alkyl groups of the radicals $R^9$ and $R^{10}$ can be branched or preferably straight-chain and are, for example, butyl, propyl, ethyl and in particular methyl.

Typical examples of monomers from which the structural elements of the formulae III and IV are derived are styrene, α-methylstyrene, methyl acrylate or methyl methacrylate and vinyl acetate.

Particularly preferably, monomers from which the structural elements of the formula II are derived are 4-(2'-trimethylsilyl-2'-propoxycarbonyloxy)styrene, 4-(2'-trimethylsilyl-2'-propoxycarbonyloxy)-α-methyl styrene and 4-(1',1'-bistrimethylsilylethoxycarbonyloxy)-α-methyl styrene.

The organometal-containing polymers according to the invention having groupings of the formula I can be obtained either by polymerization of corresponding monomers of the formula II* already containing these groupings

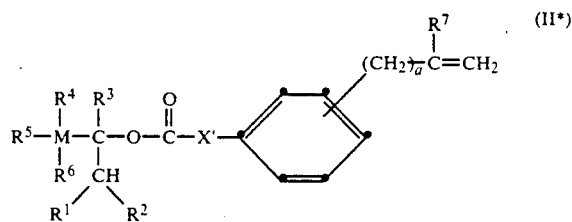

or by modification of a polymer by reaction with an organometal-containing compound of the formula I*

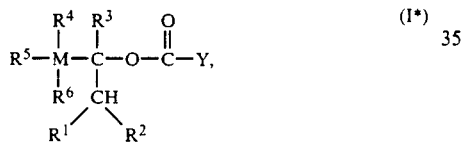

$R^1$–$R^7$, M and a in the formulae I* and II* being as defined above, X' being O, S or NH and Y being a leaving group suitable for a nucleophilic substitution.

Polymers particularly suitable for the reaction with compounds of the formula I* are those containing nucleophilic functional groups, for example hydroxyl, mercapto, amino or imido groups. This gives polymers according to the invention, in which the groupings of the formula I are bound directly or, for example, via a group of the formula V

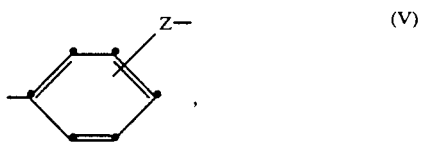

in which Z is O, S or NR' where R' is hydrogen or a single bond, to a polyalcohol, a polyphenol, a polythiol, a polyamine or a polyimide. In these polymers, the radicals X or Z of the organometal-containing grouping are O, S or NR' atoms or groups, which were present in the original unmodified polymer and were linked to the organometal-containing grouping by nucleophilic substitution of the leaving group Y of the compounds of the formula 1*. Polymers suitable for the reaction are, for example, polyvinyl alcohol, phenol novolaks or cresol novolaks, poly-4-hydroxy styrene, polymaleimide, etc.

The reaction is preferably carried out in an aprotic solvent such as toluene, tetrahydrofuran or methylene chloride, if desired, in the presence of a base, for example of a tertiary amine such as pyridine or dimethylaniline.

The polymerization or copolymerization of the organometal-containing monomers of the formula II* and possibly also of the momomers from which the structural elements of the formulae III and IV are derived is carried out in a manner known per se by radical or cationic polymerization, for example in the presence of catalytic amounts of 2,2'-azobisisobutyronitrile or of boron trifluoride etherate. The monomers from which the structural elements III and IV are derived are known and can be prepared in a known manner.

The organometal-containing monomers of the formula II* can be prepared either (a) directly by reaction of an organometal-containing alcohol of the formula VI

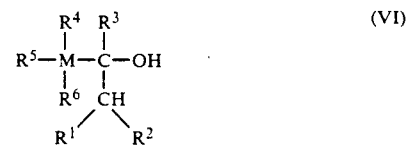

with a chloroformic acid derivative of the formula VIIa

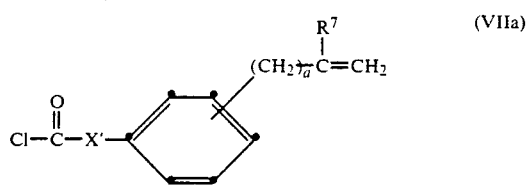

or by reaction of an organometal-containing chloroformate of the formula IX

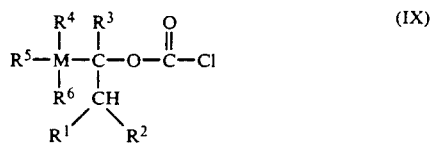

with a compound of the formula Xa

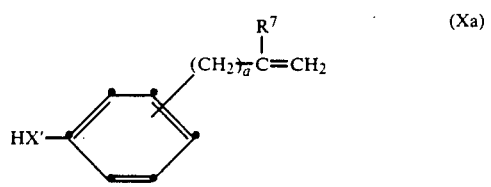

or (b) via the corresponding carbonyl compounds by reaction of the organometal-containing alcohol of the formula VI with a chloroformic acid derivative of the formula VIIb

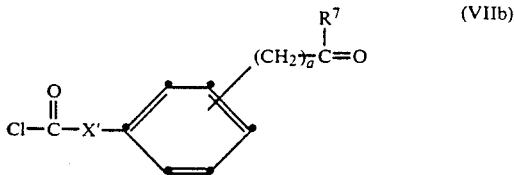

to give the carbonyl compound of the formula VIII

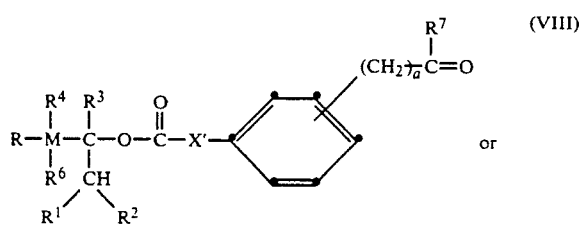

by reaction of the organometal-containing chloroformate of the formula IX with a compound of the formula Xb

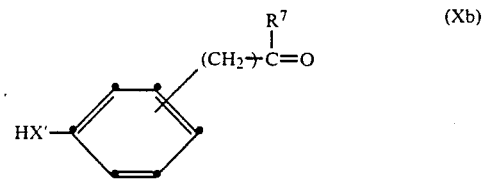

to give the compound of the formula VIII followed by a Wittig reaction of the carbonyl compound of the formula VIII with a phosphorus ylide, the symbols $R^1$ to $R^7$, M, X′ and a in the formulae VI to X having the meanings given above for the formulae I and II.

Organometal-containing alcohols of the formula VI are known or can be prepared in a known manner. Thus, in J. Organomet. Chem. 49 (1973) C9–C12, the preparation of a silicon-containing alcohol by reaction of trimethylchlorosilane with acetone is described. Organometal-containing alcohols of the formula VII can also be prepared as described in J. Org. Chem. 45 (1980) 3571–3578, in Zh. Obshch. Khim. 36 (1966) 1709 in Tetrahedron Lett. 1976, 1591–1594 or in J. Organomet. Chem. 1981, 33–47 or by an analogous procedure.

Chloroformic acid derivatives of the formula VII are also known and can be prepared, for example, by reaction of phosgene with a substituted phenol, thiophenol or aniline of the formula X, preferably in the presence of a base, for example of a tertiary amine such as pyridine or dimethylaniline. In an analogous manner, it is also possible to synthesize organometal-containing chloroformates of the formula IX by reacting an alcohol of the formula VI with phosgene. A preparative method of chloroformic acid derivatives of the formula VIIa is described, for example, in Angew. Makromol. Chem. 60/61 (1977) 125–137 or in German Offenlegungsschrift No. 2,508,512. Chloroformic acid derivatives of the formula IIIa can also be prepared by reaction of the corresponding compounds of the formula VIa with phosgene, as described, for example, in German Patent No. 1,193,031. A plurality of suitable syntheses of chloroformic acid derivatives, for example of chloroformates, and also reaction products thereof with alcohols, thiols and amines are described, for example, in Chem. Rev. 64 (1964) 645–687.

Compounds of the formula X are known and are in general commercially available.

The organometal-containing carbonyl compounds of the formula VIII were developed for the preparation of the polymers according to the invention having structural units of the formula II. They can be converted to styrene derivatives of the formula II*, for example, by means of a Wittig reaction in a known manner by reaction with a phosphorus ylide. Suitable phosphorus ylides can be prepared, for example, by reaction of a methyltriarylphosphonium salt such as methyltriphenylphosphonium bromide with a strong base such as sodium hydride or potassium tert-butylate. Wittig reactions have been described in many reviews, for example in House "Modern Synthetic Reactions", 2nd Ed., pages 682–709, W. A. Benjamin Inc., Menlo Park CA, U.S.A., 1972.

Leaving groups Y of the compounds of the formula I* suitable for a nucleophilic substitution are known. The most important requirement in selecting a leaving group is that this leaving group is less nucleophilic than the functional groups of the polymers with which it will be reacted.

Particularly suitable leaving groups Y of the compounds of the formula I* are phenoxy radicals substituted by electron acceptor groups or five-or six-membered heterocycles containing at least one, preferably two, heteroatoms, for example O, S and in particular N atoms in the ring, which are bound to the carbonyl group in the molecule via one of these heteroatoms. Examples of suitable radicals Y are, for example, 1-imidazolyl or a group of the formula XI

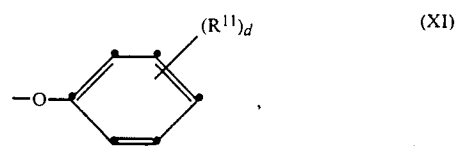

in which $R^{11}$ is halogen, in particular fluorine, chlorine or bromine, $NO_2$, CN or $CF_3$ and d is a whole number from 1 to 5, preferably from 1 to 3. A particularly suitable radical of the formula XI is 4-nitrophenoxy.

Compounds of the formula I* can be prepared in a manner known per se, for example by reaction of the organometal-containing chloroformates of the formula IX with a compound of the formula XII

YH            (XII)

Another suitable synthetic route is the reaction of the organometal-containing alcohols of the formula VI with a chloroformic acid derivative of the formula XIII

or with a carbonyl compound of the formula XIV

the compounds of the formulae VI and IX and also Y in the formulae XII, XIII and XIV being as defined above.

The compounds of the formulae XIII or XIV can be prepared, for example, by reaction of phosgene with a compound of the formula XII.

The compounds of the formula XII are known and in general commercially available.

The synthetic route via compounds of the formula XIV in the preparation of compounds of the formula I* is particularly suitable, if Y is one of the abovementioned heterocyclic radicals. A suitable compound of the formula XIV is, for example, 1,1'-carbonyldiimidazole.

The polymers according to the invention are highly suitable for use as radiation-sensitive, dry-developable recording material. As already mentioned, the polymers having groupings of the formula I can be used for the preparation of negative- or preferably positive-working photoresist systems.

Accordingly, the invention also relates to radiation-sensitive, dry-developable compositions containing an organometal-containing polymer according to the invention having side chains of the formula I and a compound liberating an acid under the influence of radiation.

A large number of compounds are known as radiation-sensitive components which form or eliminate acid under the influence of light. Among them are, for example, diazonium salts, such as are used in diazotype, o-quinone diazides, such as are used in known positive-working copying materials, or even halogen compounds which form hydrohalic acid upon irradiation. Compounds of this type are described, for example, in U.S. Pat. Nos. 3,515,552, 3,536,489 or 3,779,778 and also in German Offenlegungsschriften Nos. 2,718,259, 2,243,621 or 2,610,842.

However, cationic photoinitiators from the group consisting of iodonium or sulfonium salts are also suitable for use as radiation-sensitive components of the compositions according to the invention. These compounds are described, for example, in "UV-Curing, Science and Technology" (Editor: S. P. Pappas, Technology Marketing Corp., 642 Westover Road, Stamford, Conn., U.S.A.).

In particular, diaryliodosyl salts can also be used. These compounds are described, for example, in EP-A No. 106,797.

Furthermore, sulfoxonium salts can be used as radiation-sensitive compounds. These salts are described, for example, in EP-A Nos. 35,969, 44,274 and 54,509. These salts are in particular aliphatic sulfoxonium salts which absorb in the far UV.

In particular, it is also possible to use compounds which liberate sulfonic acids upon irradiation with actinic light. These compounds are known per se and described, for example, in GB-A No. 2,120,263, EP-A Nos. 84,515, 37,512 or 58,638 and in U.S. Pat. Nos. 4,258,121 or 4,371,605.

In the case where salts are used as radiation-sensitive, acid-eliminating components, these salts are preferably soluble in organic solvents. Particularly preferably, these salts are precipitation products containing complex acids, for example fluoroboric acid, hexafluorophosphoric acid or hexafluoroarsenic acid, or perfluoroalkanesulfonic acids such as trifluoromethanesulfonic acid. Suitable salts are, for example, diphenyliodonium, triphenylsulfonium or 4-phenylthiophenyldiphenylsulfonium hexafluoroarsenate or diphenyliodonium trifluoromethanesulfonate.

The amount of radiation-sensitive component of the compositions according to the invention can be varied in wide limits, depending on the nature and composition of the radiation-sensitive mixture. Favourable results are obtained by using about 1 to 20% by weight, preferably 3 to 15% by weight, in particular 5 to 10% by weight, of the acid-eliminating component, relative to the polymer. Since the radiation-sensitive component (initiator) remains in the system after the dry development, preferably as little as possible of these substances is used to avoid adverse influences in further process steps. Preferably, radiation-sensitive initiators are used which are completely removed during the dry development.

The compositions according to the invention can contain further conventional additives, for example stabilizers, sensitizers, for example polycyclic aromatics such as pyrene, anthracene or perylene, or dyestuffs suitable as sensitizers, for example acridines, customary polymers such as polystyrene or polymethyl methacrylate, pigments, dyes, fillers, adhesion promoters, flow-improving agents, wetting agents and plasticizers. Furthermore, for application the compositions can be dissolved in suitable solvents.

The compositions according to the invention are highly suitable for use as coating agents for substrates of any type, for example wood, textiles, paper, ceramics, glass, plastics such as polyester, polyethylene terephthalate, polyolefins or cellulose acetate, in particular in the form of films, and also of metals such as Al, Cu, Ni, Fe, Zn, Mg or Co, and of semiconductor materials such as Si, $Si_3N_4$, $SiO_2$, GaAs, Ge, etc. to which an image is to be applied by imagewise exposure. The present invention further relates to the use of the compositions according to the invention for the preparation of structured positive images and also to the substrates coated by the compositions.

The preparation of the coated substrates can be carried out, for example, by preparing a solution or suspension of the composition. Suitable solvents are all too polar and not too low boiling solvents, for example ethers, ketones or aromatics such as tetrahydrofuran, dioxane, cyclohexanone, benzene or toluene. Preference is given to 1-20%, in particular 5-15%, polymer solutions. The solution is applied to a substrate uniformly by means of known coating processes, for example by spin coating, dip coating, knife coating, curtain coating, brush coating, spray coating and reverse roll coating. It is also possible to apply the light-sensitive layer to a temporary flexible base and then to coat the final substrate, for example a silicon wafer, by layer transfer via lamination.

The amount applied (coating thickness) and the type of substrate (coating base) depend on the desired field of application. It is particularly advantageous that the compositions according to the invention can be employed in very thin layers and are notable for excellent resolution. By selecting an appropriate radiation source and radiation-sensitive component, they can be used for a wide range of applications in which the production of structured images is desirable. However, it is particularly advantageous to use them in submicron lithography and also in multi-layer lithography in which today the microelectronic requirements of a resist system are particularly high. For this reason, film coating thicknesses are preferably 0.3-2.0 μm.

After coating, the solvent is usually removed by drying, which produces an amorphous coating of the resist on the base.

If desired, another layer can be applied between base and resist. This so-called planarizing resin makes it possible to apply extremely thin homogeneous resist layers on a base having topographical features. In practice, any organic polymer or oligomer which can be applied as a polymer solution to a base is suitable. Examples of these are polyimides, polyamide acids, polymethyl methacrylate, novolaks or else other resist systems.

The radiation-sensitive layer is subjected in a conventional manner imagewise to a suitable type of radiation. The exposed areas of this layer decompose upon heat treatment into $CO_2$, the very volatile compound

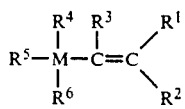

and the radical

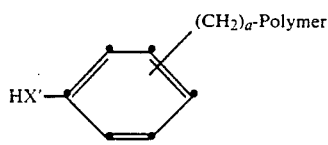

After evaporation of the very volatile compound, the exposed areas are thus free from metal-containing groupings. By means of an oxygen plasma, these metal-free areas can be developed, while the unexposed areas which still contain metal-containing groupings are resistant to the oxygen plasma. An advantage of the system according to the invention is that no solvent has to be used in this clean and residue-free dry development and that positive images of very high resolution are obtained.

For the heating for removing the volatile decomposition products after the exposure step, temperatures are preferably between 70° C. and 120° C. over a period of 1–60, in particular 5–30, minutes.

Irradiations using actinic radiation are carried out through a quartz mask containing a predetermined pattern or by means of a laser beam moving for example under computer control across the surface of the coated substrate.

Preferably, UV radiation (200–450 nm), electron beams, X-rays or ion beams are used for irradiation.

An additional distinction of the system according to the invention compared with the prior art is its unexpectedly high sensitivity for the same coating thickness. Thus, the desired result is obtained using no more than, for example, 1–10 mJ/cm².

The examples which follow illustrate the invention in more detail.

EXAMPLE 1

2-Trimethysilyl-2-propanol 83 g (12 mol) of lithium powder are initially introduced under nitrogen into a 10 l vessel equipped with ground joints and a mechanical stirrer. 6 l of the dry THF are added, and the mixture is cooled to 0° C. 1,500 g of trimethylchlorosilane (13.8 mol) and 313 g of acetone (5.4 mol) are mixed and are added dropwise using a dropping funnel to the lithium suspension. During the addition, the reaction temperature should be 0° C. After the addition, the cooling is removed and the mixture is stirred at 50° C. for 1–2 hours. The salt and excess lithium are removed from the solution. The residue is washed with n-pentane, and the filtrate is concentrated by first removing the solvent at atmospheric pressure through a mirrorcoated packed column. The trimethylsilyl ether of 2-trimethysilyl-2-propanol is then recovered at 20 mbar. This gives 300 g (28%) of a colourless liquid of boiling point 47°–48° C.

¹H-NMR ($CCl_4$): 0 ppm (s, 9H) ($H_3C$)$_3$Si-C, 0.1 ppm (s, 9H) ($H_3C$)$_3$Si-O, 1.3 ppm (s, 6H) ($H_3C$)$_2$C.

| Elemental analysis: | Calculated | Found |
|---|---|---|
| % C | 52.8 | 51.6 |
| % H | 11.8 | 11.7 |

232 g of the trimethylsilyl ether are dissolved in 900 ml of diethyl ether, and 700 ml of 15% HCl are added to this solution. The 2-phase mixture is refluxed for about one hour with vigorous stirring. The organic phase is separated off, washed once with water and then throughly with sodium bicarbonate solution, dried, and the ether is evaporated at atmospheric pressure. The residue is distilled through a packed column at 100 mbar. This gives 63 g (65%) of a clear liquid which distils at 65° C. and has a purity of more than 97% by GC.

¹H-NMR ($CCl_4$): 0 ppm (s, 9H) ($H_3C$)$_3$Si, 1.1 ppm (s, 6H) ($H_3C$)$_2$C, 1.7 ppm (s, 1H) HO—.

| Elemental analysis: | Calculated | Found |
|---|---|---|
| % C | 54.48 | 54.19 |
| % H | 12.19 | 11.98 |

EXAMPLE 2

4-(2'-Trimethylsilyl-2'-propoxycarbonyloxy)styrene 244 g (2 mol) of 4-hydroxybenzaldehyde and 2 l of 2M phosgene solution in toluene (4 mol of phosgene) are initially introduced under nitrogen into a 5 l vessel equipped with ground joints and a mechanical stirrer and thermometer. At −5° C., 242 g (2 mol) of dimethylaniline are added dropwise. After the dropwise addition is completed, stirring is continued at 0° C. for 2 hours. The mixture is allowed to warm to room temperature, excess phosgene is driven off using nitrogen, and the mixture is poured into icewater. The organic phase is throughly washed with diluted hydrochloric acid and dried with sodium sulfate. The solvent is distilled off on a rotatory evaporator. The residue is distilled in a high vacuum. This gives 250 g (68%) of 4-(chlorocarbonyloxy)benzaldehyde, a clear liquid which boils at 84° C./0.2 mbar. Upon cooling, the liquid solidifies; the melting point is slightly above room temperature.

| Elemental analysis: | Calculated | Found |
|---|---|---|
| % C | 52.06 | 51.07 |
| % H | 2.73 | 2.74 |
| % Cl | 19.21 | 21.26 |

43 g (233 mmol) of this chloroformate are dissolved in 30 ml of methylene chloride and added dropwise under nitrogen to a solution of 30.8 g (233 mmol) of 2-trimethylsilyl-2-propanol and 18.4 g of pyridine (233 mmol) in 120 ml of methylene chloride. During the addition, the temperature of the solution is kept at ≦5° C. After the dropwise addition is completed, the mixture is allowed to warm to room temperature. The mixture is left to stand under nitrogen for 12 hours, the salt is separated off, and the organic phase is washed with diluted hydrochloric acid, water and sodium bicarbonate solution. The organic phase is dried and freed from the solvent. The residue is chromatographed over silica gel using chloroform as the eluant. This gives 30.6 g (46%) of 4-(2′-trimethylsily-2′-propyloxycarbonyloxy)-benzaldehyde as a colourless liquid.

$^1$H-NMR (acetone-d$_6$): 0.1 ppm (s, 9H) (H$_3$C)$_3$Si, 1.5 ppm (s, 6H) (H$_3$C)$_2$C, 7.3–7.9 ppm (m, 4H) H-Ar, 10 ppm (s, 1H) CHO.

| Elemental analysis: | Calculated | Found |
| --- | --- | --- |
| % C | 59.97 | 59.62 |
| % H | 7.19 | 7.18 |
| % Si | 10.01 | 9.95 |

The benzaldehyde derivative is converted to the corresponding styrene derivative by means of a Wittig reaction: 38.6 g (108 mmol) of methyltriphenylphosphonium bromide in 400 ml of dry THF are initially introduced into a 1 l 3-neck round-bottomed flask equipped with dropping funnel and thermometer. 12.2 g (108 mmol) of potassium tert-butylate are added, and the mixture is stirred under nitrogen at room temperature for 1 hour. 20 g (72 mmol) of benzaldehyde derivative dissolved in 180 ml of THF are then added dropwise at room temperature. After 15 hours, the TLC (toluene/hexane=1:1) shows only the product. The mixture is poured onto ice and extracted twice with n-hexane. The organic phase is washed twice with water, dried and evaporated. The residue is chromatographed over a silica gel column using toluene/hexane=1:1. This gives 13 g (65%) of a colourless liquid which can be distilled in a high vacuum (boiling point 110° C./0.05 mbar).

$^1$H-NMR (acetone-d$_6$): 0.05 ppm (s, 9H) (H$_3$C)$_3$Si, 1.45 ppm (s, 6H) (H$_3$C)$_2$C, 5.1–5.8 ppm (m, 2H) H$_2$C=, 6.5–6.8 ppm (m, 1H) =CH—, 7.0–7.5 ppm (m, 4H) H-Ar.

| Elemental analysis: | Calculated | Found |
| --- | --- | --- |
| % C | 64.71 | 63.95 |
| % H | 7.97 | 7.91 |
| % Si | 10.09 | 10.24 |

EXAMPLE 3

4-(2′-Trimethylsilyl-2′-propoxycarbonyloxy)-α-methyl styrene

This monomer is prepared starting from 4-hydroxyacetophenone exactly in the same manner as the styrene derivative described in Example 2. The yields and physical data of the compounds prepared are as follows:

4-(Chlorocarbonyloxy)acetophenone

Yield 82%, melting point 33° C.
$^1$H-NMR (CDCl$_3$): 2.6 ppm (s, 3H)

7.25–8.10 ppm (m, 4H) H-Ar.

| Elemental analysis: | Calculated | Found |
| --- | --- | --- |
| % C | 54.43 | 54.41 |
| % H | 3.55 | 3.59 |
| % Cl | 17.85 | 17.78 |

4-(2′-Trimethylsilyl-2′-propoxycarbonyloxy)acetophenone

Yield 68%, melting point 41° C.
$^1$H-NMR (acetone-d$_6$): 0.1 ppm (s, 9H) (H$_3$C)$_3$Si, 1.5 ppm (s, 6H) (H$_3$C)$_2$C, 2.6 ppm (s, 3H)

7.25–8.1 ppm (m, 4H) H-Ar.

| Elemental analysis: | Calculated | Found |
| --- | --- | --- |
| % C | 61.19 | 60.90 |
| % H | 7.53 | 7.48 |

4-(2′-Trimethylsilyl-2′-propoxycarbonyloxy)-α-methyl styrene

Yield 53%, boiling point 118° C./0.04 mbar.
$^1$H-NMR (acetone-d$_6$): 0.1 ppm (s, 9H) (H$_3$C)$_3$Si, 1.5 ppm (s, 6H) (H$_3$C)$_2$C, 2.1 ppm (m, 3H)

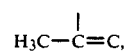

5.1–5.4 ppm (m, 2H) H$_2$C=C<, 7.1–7.6 ppm (m, 4H) H-Ar.

| Elemental analysis: | Calculated | Found |
| --- | --- | --- |
| % C | 65.71 | 65.77 |
| % H | 8.27 | 8.30 |

EXAMPLE 4

(Poly[4-(2′-trimethylsilyl-2′-propoxycarbonyloxy)styrene]

10 g (36 mmol) of 4-(2′-trimethylsilyl-2′-propoxycarbonyloxy)styrene (prepared according to Example 2) are dissolved in 20 ml of toluene, and 1 mol % of 2,2′-azobisisobutyronitrile is added to this solution. The solution is freed from oxygen and polymerized at 70° C. under nitrogen. After several hours, the viscous solution is diluted with 50 ml of methylene chloride and poured into 500 ml of methanol. The precipitated polymer is again dissolved in methylene chloride and reprecipitated in methanol. The polymer is dried at 50° C. in the high vacuum. Yield 6 g (60%).

$^1$H-NMR (CDCl$_3$): 0.1 ppm (s, 9H) (H$_3$C)$_3$Si, 0.75–2.25 (m/s, 9H)

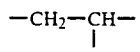

and $(H_3C)_2C$, 6.2–7.1 ppm (m, 4H) H-Ar.

| Elemental analysis: | Calculated | Found |
|---|---|---|
| % C | 64.71 | 64.75 |
| % H | 7.96 | 7.92 |

Using gel permeation chromatography (GPC) in tetrahydrofuran with polystyrene as a standard, a molecular weight of $\overline{M}_n = 42,000$ and $\overline{M}_w = 87,000$ is found.

Thermogravimetric analysis: at a heating rate of 4° C./min. in air, the weight loss is about 10% at 160° C. At 175° C., the compound is completely decarboxylated. The weight loss is 55%, which exactly corresponds to the elimination of $CO_2$ and of isopropenyltrimethylsilane.

EXAMPLE 5

Poly[4-(2'-trimethylsilyl-2'-propoxycarbonyloxy)-α-methyl styrene]

In a 100 ml round-bottomed flask equipped with a glass attachment, 20 g (68 mmol) of the monomer are dissolved in 60 ml of methylene chloride. The oxygen is removed from the solution, and 1.1 ml of a 1M solution of $BF_3.Et_2O$ in methylene chloride are added under nitrogen at −78° C. The polymerization is then allowed to proceed at −20° to −40° C. After 18 hours, the viscous solution is poured into 1 liter of methanol. The precipitated polymer is separated off, dried and again dissolved in methylene chloride and precipitated in methanol. It is then dried at 50° C. in the high vacuum. This gives 13 g (65%) of the polymer.

$^1$H-NMR (CDCl$_3$): 0.1 ppm (s, 9H) (H$_3$C)$_3$Si, 1.0–2.1 ppm (m/s, 11H) H$_3$C—C, —CH$_2$—, H$_3$C—C—CH$_3$, 6.4–1.2 ppm (m, 4H) H-Ar.

| Elemental analysis: | Calculated | Found |
|---|---|---|
| % C | 65.71 | 65.73 |
| % H | 8.27 | 8.20 |
| % Si | 9.60 | 9.68 |

GPC measurements in THF show a $\overline{M}_n$ of 33,000 and a $\overline{M}_w$ of 84,000.

TGA analysis: at a heating rate of 4° C./minute in air, the weight loss is about 10% at 155° C. and about 53% at 171° C. The weight loss of 53% corresponds to the complete elimination of $CO_2$ and isopropenyltrimethylsilane.

EXAMPLE 6

4-(2'-Trimethylsilyl-2'-propoxycarbonyloxy)nitrobenzene 10 g (76 mmol) of 2-trimethylsilyl-2-propanol, 6 g (76 mmol) of pyridine and 30 ml of methylene chloride are initially introduced under nitrogen into a 100 ml glass flask equipped with a thermometer, dropping funnel and magnetic stirrer, and the solution is cooled to 0° C. 15.2 g (76 mmol) of 4-nitrophenyl chloroformate are dissolved in 20 ml of methylene chloride and are added dropwise to the solution initially introduced at such a rate that the temperature remains between 0° C. and 5° C. After the dropwise addition is completed, the mixture is allowed to warm to room temperature and stirring is continued for about another hour. The mixture is poured into ice water, the organic phase is washed with 1N HCl and then with NaHCO$_3$. The dried organic phase is concentrated, and the residue is recrystallized from n-hexane. This gives 10 g (44%) of a crystalline substance of melting point 61° C.

$^1$H-NMR (acetone-d$_6$): 0.1 ppm (s, 9H) (H$_3$C)$_3$Si, 1.55 ppm (s, 6H) (H$_3$C)$_2$C, 7.4–8.1 ppm (m, 4H) H-Ar.

| Elemental analysis: | Calculated | Found |
|---|---|---|
| % C | 52.51 | 52.31 |
| % H | 6.44 | 6.41 |
| % N | 4.71 | 4.60 |

EXAMPLE 7

1-(2'-Trimethylsilyl-2'-propoxycarbonyl)imidazole 10 g (76 mmol) of 2-trimethylsilyl-2-propanol, 14.7 g (91 mmol) of 1,1'-carbonyldiimidazole and 50 ml of methylene chloride are initially introduced under nitrogen into a sulfonating flask equipped with cooler, thermometer and magnetic stirrer. The mixture is then stirred under reflux for 21 hours. The mixture is poured into ice water, the phases are separated, and the organic phase is washed twice with water. The organic phase is dried, concentrated on a rotary evaporator, and the residue is distilled in a high vacuum. This gives 11.3 g (66%) of a colourless liquid of boiling point 90° C./0.1 mbar.

$^1$H-NMR (acetone-d$_6$): 0.2 ppm (s, 9H) (H$_3$C)$_3$Si, 1.6 ppm (s, 6H) (H$_3$C)$_2$C, 7.74 and 8.1 ppm (s, 3H) H-imidazole.

| Elemental analysis: | Calculated | Found |
|---|---|---|
| % C | 53.06 | 52.31 |
| % H | 8.02 | 8.02 |
| % N | 12.38 | 12.40 |

EXAMPLE 8

4-(1',1'-Bistrimethylsilylethoxycarbonyloxy)-α-methyl styrene

The condensation reaction between 4-(chlorocarbonyloxy)acetophenone and 1,1-bistrimethylsilylethanol (prepared according to Tetrahedron Lett., 1976, 1591–1594) in methylene chloride proceeds analogously to the condensation described in Example 2. Purification by column chromatography gives a solid which can be recrystallized from hexane.

4-(1',1'-Bistrimethylsilylethoxycarbonyloxy)acetophenone

Yield 60%, melting point 79.5° C.

$^1$H-NMR (CDCl$_3$): (CH$_3$)$_3$Si (18H, s): 0.12 ppm, CH$_3$—C (3H, s): 1.6 ppm, CH$_3$—C=O (3H, s): 2.6 ppm, H-Ar (4H, m): 7.2–8.05 ppm.

| Elemental analysis: | Calculated | Found |
|---|---|---|
| % C | 57.91 | 58.01 |
| % H | 8.01 | 8.13 |
| % Si | 15.93 | 15.92 |

4-(1',1'-Bistrimethylsilylethoxycarbonyloxy)-α-methylstyrene

The Wittig reaction is carried out analogously to Example 2. Purification by column chromatography gives a colourless liquid in a yield of 41%.

$^1$H-NMR (CDCl$_3$): (CH$_3$)$_3$Si (18H, s): 0.15 ppm, CH$_3$—C (3H, s): 1.6 ppm, CH$_3$—C= (3H, m): 2.15 ppm, CH$_2$=C (2H, m): 5.04–5.33 ppm, H-Ar (4H, m): 7.00–7.53 ppm.

| Elemental analysis: | Calculated | Found |
|---|---|---|
| % C | 61.66 | 61.57 |
| % H | 8.63 | 8.77 |
| % Si | 16.02 | 16.08 |

EXAMPLE 9

Poly[4-(1',1'-bistrimethylsilylethoxycarbonyloxy)-α-methylstyrene]

In a 250 ml round-bottomed flask equipped with magnetic stirrer, 20 g (57 mmol) of 4-(1',1'-bistrimethylsilylethoxycarbonyloxy)-α-methylstyrene (prepared according to Example 8) are dissolved in 60 ml of anhydrous methylene chloride and are freed from oxygen on a vacuum/nitrogen line using the freezing/thawing technique. The solution is cooled to minus 60° C., and 1.2 mmol of freshly distilled BF$_3$.Et$_2$O are added. The solution is allowed to polymerize between minus 60° C. and minus 40° C. for 18 hours. The polymer is precipitated by pouring the viscous solution into 1 l of methanol. The white polymer powder is dried and dissolved in 100 ml of THF, the solution is filtered and the polymer is again precipitated by pouring the filtrate into 1 l of methanol. The polymer is separated off, sucked dry in air and dried at 50° C. in a high vacuum.

Yield: 6.1 g of a white polymer powder (31%).

| Elemental analysis: | Calculated | Found |
|---|---|---|
| % C | 61.66 | 61.60 |
| % H | 8.63 | 8.62 |
| % Si | 16.02 | 16.03 |

GPC (THF): $\overline{M}_n$=52,000, $\overline{M}_w$=102,000.

Thermogravimetric analysis: The polymer decomposes at 170° C. into CO$_2$ and 1,1-bistrimethylsilylethylene.

EXAMPLE 10

Preparation of 4-(2'-trimethylsilyl-2'-propoxycarbonyloxy)-α-methylstyrene by reaction of 2-trimethylsilyl-2-propanol with 4-chloroformyloxy-α-methylstyrene In a 250 ml three-necked flask equipped with dropping funnel and thermometer, 10 g (75.6 mmol) of 2-trimethylsilyl-2-propanol and 7.2 g (91 mmol) of pyridine are dissolved in 100 ml of anhydrous methylene chloride. After the solution has been cooled to 0° C., 17.8 g (90.5 mmol) of 4-chloroformyloxy-α-methylstyrene (prepared according to Example 6.2 of German Offenlegungsschrift No. 2,508,512) are added dropwise. After the dropwise addition is completed, the suspension is allowed to warm to room temperature and stirred for another hour. The resulting pyridine hydrochloride is separated off, and the organic phase is thoroughly washed two times each with 1N HCl, water and saturated sodium bicarbonate solution. It is then dried with sodium sulphate and concentrated on a rotary evaporator. The liquid product is purified over a silica gel column using toluene as the eluant. This gives 14 g (40 mmol, a yield of 63%) of 4-(2'-trimethylsilyl-2'-propoxycarbonyloxy)-α-methylstyrene whose properties are identical to those of the substance described in Example 3.

APPLICATION EXAMPLES

Example A1

10% by weight of 4-phenylthiophenyldiphenylsulfonium hexafluoroarsenate [prepared according to J. Polymer Sci., Polymer Chem. Ed., 18, 2677–2695 (1980)], relative to the polymer of Example 4, are added to a 10% by weight solution of this polymer in cyclohexanone. This solution is added dropwise through a 0.5 micron filter onto a silicon wafer and a homogeneous film is produced by spin coating. The polymer film is dried at 90° C. over a period of 20 minutes. The coating thickness of the amorphous, homogeneous film is 0.5 μm. Through a chromium/quartz mask, the film is exposed at 254 nm to an intensity of 1-2 mJ/cm$^2$. The exposed material is then developed at 90° C. for 10 minutes. The highly resolved masked pattern can be easily recognized. The exposed zones are completely removed by etching under anisotropic conditions in an oxygen plasma (O$_2$ flow: 20 sccm/min, pressure: $4\times10^{-2}$ mbar, 35 watt) using an RIE instrument (reactive ion etching), while the unexposed zones are not attacked. Measurements showed that exposed zones are etched off about 30 times faster than unexposed zones. Using this technique, it is possible to dry-develop even submicron structures in the resist.

Example A2

5% by weight of diphenyliodonium trifluoromethanesulfonate (prepared according to German Offenlegungsschrift No. 2,731,396, Example 4), relative to the polymer of Example 5, are added to a 10% by weight solution of this polymer in cyclohexanone. The solution is applied to a silicon wafer as described in Example A1 to give a resist film, 0.7 μm thick. The film is exposed through a chromium/quartz mask at 254 nm to an intensity of 4 mJ/cm$^2$ and then developed at 90° C. over a period of 10 minutes. The poly[(4-hydroxy)-α-methylstyrene] formed in the exposed zones is dissolved off using an aqueous/alkaline developer containing 1 part of Microposit MF 315 ® (from Shipley Co. Inc., Newton, Mass., U.S.A.), 1 part of deionized water and 1 part of isopropanol, while the unexposed zones are not attacked by the basic developer. In this manner, it is possible to produce unswollen patterns of high resolution in the resist film.

Example A3

5% by weight of 4-phenylthiophenyldiphenylsulfonium hexafluoroarsenate, based on the polymer of Example 5, are added to a 10% by weight solution of this polymer in cyclohexanone. The solution is applied to a crosslinked polyimide layer (Probimid ® 284 from Ciba-Geigy AG), 2.3 μm in thickness, as described in Example A1, to produce a resist film, 0.7 μm in thickness. The film is exposed through a chromium/quartz mask at 254 nm to an intensity of 10 mJ/cm$^2$ and then developed at 100° C. over a period of 30 minutes. The exposed zones freed from silicon are etched off under anisotropic conditions (plasma flow: 20 sccm/min; gases: CF$_4$ for one minute, then O$_2$; pressure 4×10$^{-2}$ mbar, 35 watt) using an RIE instrument together with the underlying polyimide layer, while the unexposed zones are plasma-resistant.

What is claimed is:

1. A composition comprising (a) a polymer having groupings of the formula I $$R^5-\underset{\underset{\underset{R^1}{CH}}{R^6}}{\overset{\overset{R^4}{|}}{\underset{|}{M}}}-\overset{R^3}{\underset{|}{C}}-O-\overset{O}{\underset{||}{C}}-X- \quad (I)$$

in which R$^1$ to R$^6$ independently of one another are C$_1$-C$_4$alkyl, C$_1$-C$_4$alkoxy, phenyl, benzyl, phenoxy, a group —M(R$^8$)$_3$ or $$\left(\begin{array}{c}R^8\\|\\M\\|\\R^8\end{array}\right)_b R^8,$$

or R$^3$ and R$^4$ together are $$\left(\begin{array}{c}R^8\\|\\M\\|\\R^8\end{array}\right)_c$$

and R$^1$ to R$^3$ in addition are hydrogen, R$^8$ is C$_1$-C$_4$alkyl, C$_1$-C$_4$alkoxy, phenyl, benzyl or phenoxy, M is Si, Ge, Sn, CH$_2$Si or OSi and X is O, S or NR', where R' is hydrogen or a single bond, b is a whole number from 1 to 6 and c is a whole number from 3 to 6, wherein the polymer has an average molecular weight between 1,000 and 1,000,000 and (b) a compound liberating an acid under the influence of radiation.

2. A composition according to claim 1, in which M is CH$_2$Si, OSi or Si.

3. A composition according to claim 1, in which X is S or O.

4. A composition according to claim 1, in which R$^1$ and R$^2$ are each hydrogen, R$^3$ is methyl or Si(CH$_3$)$_3$ and R$^4$ to R$^6$ are each methyl or in which R$^3$ and R$^4$ together are $$+\underset{\underset{CH_3}{|}}{\overset{\overset{CH_3}{|}}{Si}}+_3 \quad \text{or} \quad +\underset{\underset{CH_3}{|}}{\overset{\overset{CH_3}{|}}{Si}}+_4.$$

5. A composition according to claim 1, in which R$^1$ and R$^2$ are each hydrogen, R$^3$ is methyl or Si(CH$_3$)$_3$, R$^4$ to R$^6$ are each methyl, M is Si and X is O.

6. A composition according to claim 1 having repeating units of the formula II $$\left[-CH_2-\underset{\underset{\underset{}{\phi}}{(CH_2)_a}}{\overset{\overset{R^7}{|}}{C}}-\right] \quad (II)$$

with substituent $R^5-\underset{\underset{\underset{R^1}{CH}{R^2}}{R^6}}{\overset{\overset{R^4}{|}}{\underset{|}{M}}}-\overset{R^3}{\underset{|}{C}}-O-\overset{O}{\underset{||}{C}}-X'-$ on the ring in which R$^1$ to R$^6$ and M are as defined in claim 1, X' is O, S or NH, R$^7$ is hydrogen or C$_1$-C$_4$alkyl and a is zero or 1.

7. A composition according to claim 6, in which a is zero and R$^7$ is hydrogen or methyl.

8. A composition comprising repeating units of the formula II according to claim 6, up to 50 mol %, relative to the entire copolymer, of structural units which are derived from other copolymerizable monomers and a compound liberating an acid under the influence of radiation.

9. A composition according to claim 8 containing, in addition to the structural elements of the formula II, at least one of the structural elements of the formulae III or IV $$\left[-CH_2-\overset{\overset{R^7}{|}}{\underset{\underset{\phi-R^9}{|}}{C}}-\right] \quad (III)$$

$$\left[-CH_2-\overset{\overset{R^7}{|}}{\underset{\underset{R^{10}}{|}}{C}}-\right], \quad (IV)$$

in which R$^7$ is as defined in claim 6, R$^9$ is hydrogen, C$_1$-C$_4$alkyl or C$_1$-C$_4$alkoxy and R$^{10}$ is hydrogen, C$_1$-C$_4$alkyl, C$_1$-C$_4$alkoxy, C$_1$-C$_4$alkoxycarbonyl or C$_1$-C$_4$alkylcarbonyloxy.

10. A composition according to claim 1, in which the groupings of the formula I are bound directly or via a group of the formula V $$\phi-Z- \quad (V)$$

in which Z is O, S or NR' where R' is hydrogen or a single bond, to a polyalcohol, a polyphenol, a polythiol, a polyamine or a polyimide.

11. Substrate coated with a composition according to claim 1.

12. Substrate coated with a composition according to claim 8.

* * * * *